United States Patent
Bulovic et al.

(10) Patent No.: US 7,345,764 B2
(45) Date of Patent: Mar. 18, 2008

(54) APPARATUS AND METHOD FOR A SLIM FORMAT SPECTROMETER

(76) Inventors: Vladimir Bulovic, 16 Lillian Rd., Lexington, MA (US) 02420; Conor Madigan, 195 Binney St., Apt. 1302, Cambridge, MA (US) 02142; Ioannis Kymissis, 8 Museum Way, #206, Cambridge, MA (US) 02141

( * ) Notice: Subject to any disclaimer, the term of this patent is extended or adjusted under 35 U.S.C. 154(b) by 370 days.

(21) Appl. No.: 11/050,692

(22) Filed: Feb. 7, 2005

(65) Prior Publication Data

US 2006/0176485 A1    Aug. 10, 2006

(51) Int. Cl.
*G01N 21/25* (2006.01)
(52) U.S. Cl. ........................... 356/419; 356/408
(58) Field of Classification Search ........ 356/318–319, 356/419
See application file for complete search history.

(56) References Cited

U.S. PATENT DOCUMENTS

| | | | | |
|---|---|---|---|---|
| 3,382,183 A | * | 5/1968 | Donoian et al. | 252/582 |
| 4,207,624 A | * | 6/1980 | Dentino et al. | 367/135 |
| 5,387,977 A | * | 2/1995 | Berg et al. | 356/407 |
| 5,627,639 A | * | 5/1997 | Mende et al. | 356/310 |
| 5,708,264 A | * | 1/1998 | Hawkins et al. | 250/226 |
| 5,828,450 A | * | 10/1998 | Dou et al. | 356/301 |
| 5,891,025 A | * | 4/1999 | Buschmann et al. | 600/331 |
| 6,078,709 A | * | 6/2000 | Abramov et al. | 385/37 |
| 6,093,349 A | * | 7/2000 | Ihara et al. | 252/584 |
| 6,297,071 B1 | * | 10/2001 | Wake | 438/70 |
| 6,373,573 B1 | * | 4/2002 | Jung et al. | 356/419 |
| 6,396,053 B1 | * | 5/2002 | Yokoi | 250/234 |
| 6,677,604 B2 | * | 1/2004 | Mitrovic | 250/573 |
| 6,825,930 B2 | * | 11/2004 | Cronin et al. | 356/328 |
| 6,915,955 B2 | * | 7/2005 | Jung et al. | 235/462.06 |
| 6,998,660 B2 | * | 2/2006 | Lyon et al. | 257/294 |
| 7,157,025 B2 | * | 1/2007 | Ichimura et al. | 252/582 |
| 2003/0038938 A1 | * | 2/2003 | Jung et al. | 356/419 |

* cited by examiner

*Primary Examiner*—Layla G. Lauchman
*Assistant Examiner*—Jarreas Underwood
(74) *Attorney, Agent, or Firm*—Duane Morris LLP

(57) ABSTRACT

Disclosed is an apparatus and method for a compact, rugged, and inexpensive spectrometer that will make possible a range of new applications for optical spectroscopy including point-of-care medical devices, personal monitors, and ubiquitous environmental sensing. Embodiments of the disclosure include silicon photodetectors where incident light passes through a layer of an inexpensive, absorbing thin film. In one embodiment, one or more photodetectors may be used where a series of absorbing thin film layers are passed over the photodetectors. In another embodiment, an absorbing thin film layer is placed over one or more photodetectors where the absorptivity of the thin film layer is different for each photodetector.

29 Claims, 8 Drawing Sheets

APPARATUS AND METHOD FOR A SLIM FORMAT SPECTROMETER

BACKGROUND

The development of compact, rugged, inexpensive optical spectrometers would benefit a range of applications, such as point-of-care medical devices, food analyzers, color sensors, field-installed chemical and environmental sensors, and personal environmental monitors. Today's most compact spectrometers utilize silicon photodetector arrays capped with interference bandpass filters; however, the high cost of fabrication of these devices make them commercially impractical.

At present, optical spectroscopy is utilized in many industrial and research settings, and the state of the art in small size and value are portable, textbook-sized units costing $3K including a PDA for monitoring the device (e.g. the SR2000, manufactured by Ocean Optics, Inc.) These units utilize a fiber input, diffractive optics, and a CCD detector mounted directly onto a PC-board, where the associated chips for signal-processing reside. While the resulting package represents a significant improvement in form factor and price-point over the alternative (table-top units costing $6K and up, e.g. the Oriel MS257 Spectrometer), these systems are still too large and expensive for use as ubiquitous sensors and personal monitors (e.g. environmental or medica).

There are currently a number of approaches being pursued in the development of micro-scale spectrometers, but each of the existing approaches has substantial drawbacks. Correia et al. (J. H. Correia et al, *Sens. and Act.*, 82, 191-97 (2000)) report a single chip CMOS microspectrometer utilizing an array of Fabry-Perot etalons with different resonance cavity lengths. In this approach the fabrication is complex and expensive, and ill suited to even high cost applications. Yee et al. (G. M. Yee et al, *Sens. and Act.*, 58, 61-66 (1997)) and Kung et al. (H. L. Kung et al, *IEEE J. Sel. Top. Quant. Elec.*, 8, 98-105 (2002)) have demonstrated rudimentary spectrometers using micromachined components (a grating in the former, a mirror in the latter) and in both cases, fabrication complexity and expense once again limit the applicability of the approaches. A number of groups, such as L. Colace et al, *Appl. Phys. Lett.*, 80, 3039-3041 (2002), have demonstrated so-called voltage-tunable photodetectors, for use as a sensing element in the wavelength stabilization of semiconductor lasers using feedback. While such devices could theoretically be used as the basis for a miniature spectrometer, again fabrication is difficult (involving a seven layer structure of InP and InGaAsP and micromachining) and expensive. Finally, Optical Coating Laboratory, Inc. has developed the manufacturing capability to produce a rectangular bragg reflector with a linearly varying pass band, with which they can construct a rugged and compact spectrometer (using an array of photodetectors) with good wavelength sensitivity and range. However, the bragg reflector strip, which consists of a multilayer dielectric stack with graded thicknesses, remains too expensive ($650 or more, depending on specifications) for low cost applications.

The present disclosure proposes a change in the detection paradigm that allows the use of silicon photodetectors capped with inexpensive, single-layer absorbing thin films. The present disclosure alleviates the need for expensive optical components (e.g., lenses and gratings) and intricate assembly during manufacturing, which are typical of existing spectrometer designs. At the same time, the ruggedness of the device is enhanced by vastly reducing the number of components and their complexity. The present disclosure describes a slim format spectrometer that would enable devices the size of handheld PDAs, for example, and ultimately smaller such as for a lab-on-a-chip application, and costing much less than the thousands of dollars of current devices, effectively rewriting the economics for field applications of optical spectroscopy. Furthermore, the active part of the spectrometer would be no larger that the detector array itself (e.g., 1 cm×1 cm×1 mm) enabling for the first time economical, small format, pervasive spectroscopy applications.

BRIEF DESCRIPTION OF THE DRAWINGS

FIG. 1(*a*) illustrates an embodiment where thin film absorbers are integrated with a detector array. FIG. 1(*b*) illustrates an embodiment where thin film absorbers are passed relative to a detector.

DETAILED DESCRIPTION

The present disclosure proposes a compact, rugged, and inexpensive spectrometer that will make possible a range of new applications for optical spectroscopy, including point-of-care medical devices, personal monitors, and ubiquitous environmental sensing. All existing commercial optical spectrometers utilize photodetectors in conjunction with interference bandpass filters or diffractive optics to achieve wavelength differentiation. In the present disclosure, the detection paradigm is changed, allowing for the use of silicon photodetectors capped, for example, with inexpensive, single-layer absorbing thin films to construct the entire spectrometer. By varying the thickness of the films (and thereby the total absorption), the wavelengths are differentiated. This approach alleviates the need for expensive optical components (e.g. lenses, interference filters, gratings) and intricate assembly during manufacturing, which are typical of existing spectrometer designs. At the same time, the ruggedness of the device is enhanced by vastly reducing the number of components and their complexity. The absorbing films may be deposited by ink-jet printing using conventional dyes, further simplifying device fabrication and allowing for leveraging the extensive knowledge-base of the printing industry in the selecting the absorbing material. Additionally, since the film patterning functionality is built into the printer, the processing becomes entirely straightforward.

Figure 1:
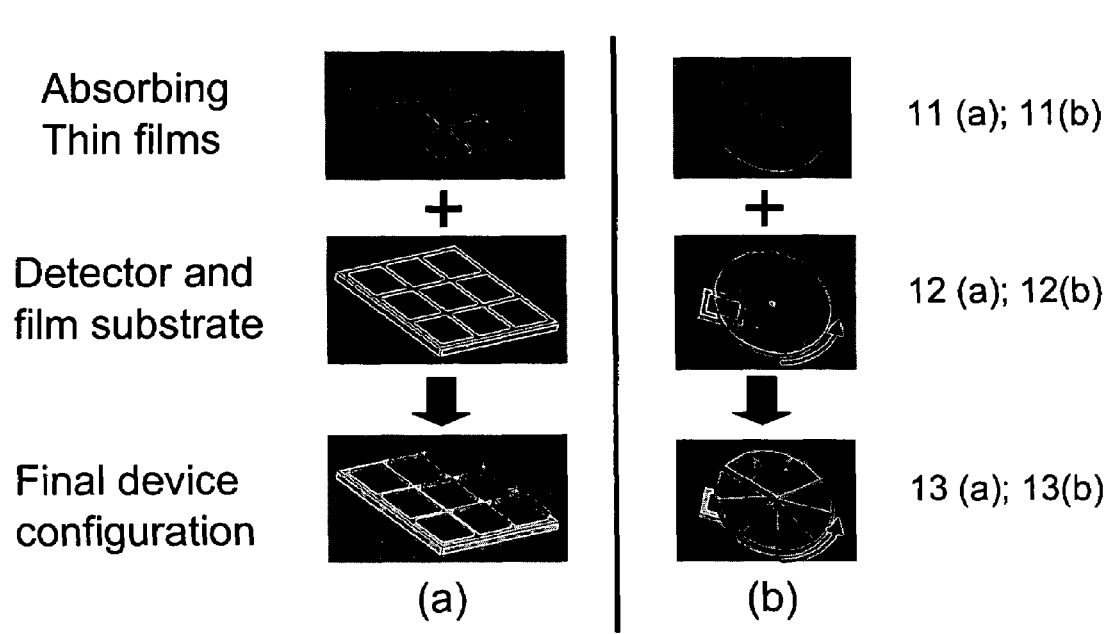
FIG. 1 illustrates two embodiments of spectrometers according to the present disclosure.

For example, two embodiments of a spectrometer as disclosed herein will be described in detail. It will be apparent to those of skill in the art that other embodiments are possible using the methodology and apparatus herein disclosed. With reference to FIG. 1, embodiments of photodetectors are shown. FIG. 1(a) illustrates an array of photodetectors 12(a), which may be silicon photodetectors, each with a thin film 11(a) coated directly onto the elements of the array to make the detector device assembly 13(a). FIG. 1(b) illustrates a single photodetector 12(b) with thin films 11(b) coated, for example, onto an independent substrate moved relative to the detector 12(b) to make the detector device assembly 13(b). For FIG. 1(a), all of the necessary measurements may be taken simultaneously. For FIG. 1(b), all of the measurements may be taken sequentially, for example as the absorber substrate is moved relative to the detector. Of the two proposed configurations, the single detector approach would most likely provide the lowest cost, while the detector array approach would theoretically provide the best miniaturization and durability due to its fully monolithic fabrication. In principle, the devices need not be any larger than the detector substrate, making possible, for instance, wafer thin, square centimeter packages.

To illustrate the principles of the device disclosed herein, one non-limiting embodiment will now be described in detail. Attention is now directed towards FIG. 2 where an embodiment with a series of thin films 21 (identified as $d_1$ through $d_n$) with identical composition and different thicknesses is depicted. Each of the thin films overlays a photodetector element 22. The photodetectors 22 are, in this embodiment, mounted on a substrate 23. The absorption spectrum of our thin film material 21 is given by an absorption coefficient, $\alpha(\lambda)$. The objective is to reconstruct the incident spectrum 24, identified as $S(\lambda)$, from the detected photocurrent signal, $D(d)$, (identified as $D(d_1)$ through $D(d_n)$) where $\lambda$ refers to the optical wavelength and d is the thin film thickness.

The conversion between $S(\lambda)$ and $D(d)$ is a simple matrix operation, for discrete $\lambda$ and d. The fraction of light transmitted, $T(\lambda, d)$, as a function of $\lambda$ and d is determined from $\alpha(\lambda)$ through Beer's law:

$$T(\lambda, d) = e^{-\alpha(\lambda) d}.$$

Then, $$\overleftrightarrow{T} \cdot \vec{S} = \vec{D}$$

where $\vec{S}$ and $\vec{D}$ are column vectors comprised respectively of $S(\lambda_i)$ and $D(d_j)$, and $\overleftrightarrow{T}$ is the transmission matrix comprised of $T(\lambda_i, d_j)$. Defining the inverse of $\overleftrightarrow{T}$, $\overleftrightarrow{T}^{-1}$, as the matrix for which, $\overleftrightarrow{T}^{-1} \cdot \overleftrightarrow{T} = I$, we can then write, $$\vec{S} = \overleftrightarrow{T}^{-1} \cdot \vec{D}$$

with which we can recover the incident spectrum $\vec{S}$ from the measured photodetector currents $\vec{D}$.

There are some restrictions on when this recovery is possible. One requirement is that $\alpha(\lambda)$ changes monotonically over the wavelength region of interest. Also, there must be at least as many different detected signals ($D(d_1)$ through $D(d_n)$) as wavelengths being resolved. Another concern is noise, as the system does not produce a linear response to random noise introduced in $\vec{D}$. In particular, care must be taken in choosing the $\alpha(\lambda)$ and $\{d_1, \ldots, d_n\}$ values to optimize the insensitivity to noise. However, for a proper design, good performance is possible.

Figure 2:
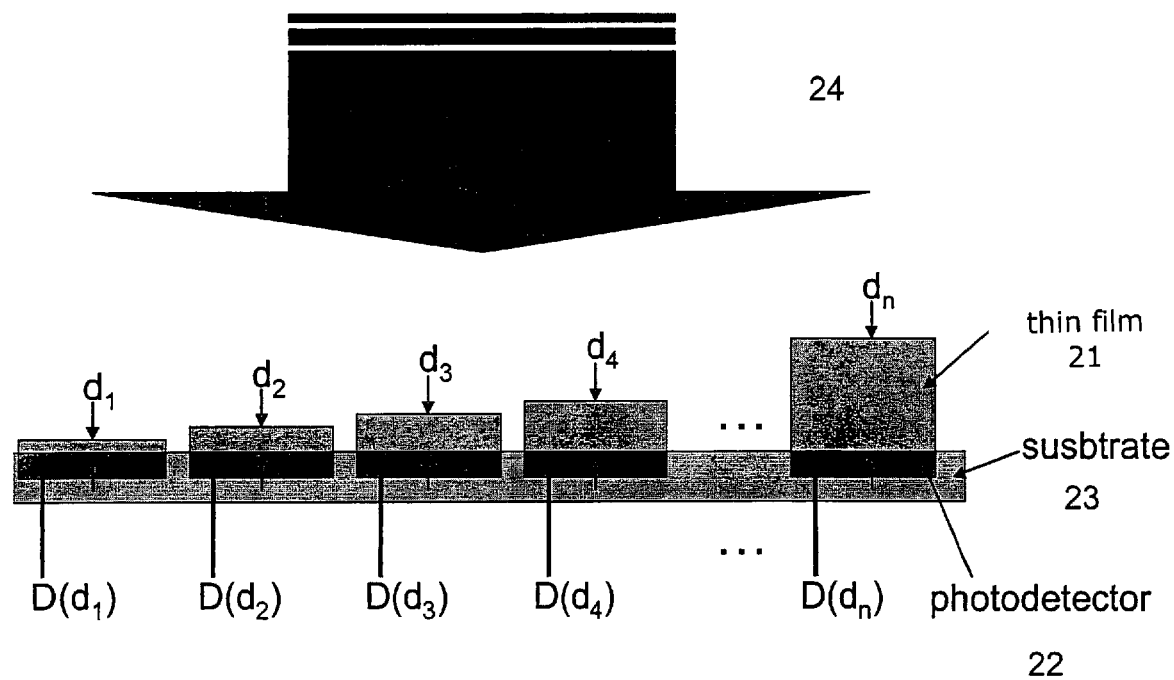
FIG. 2 illustrates a further embodiment of the present disclosure. Photodetectors are mounted on a substrate and each photodetector has a different thickness of the same absorbing thin film.
Figure 3:
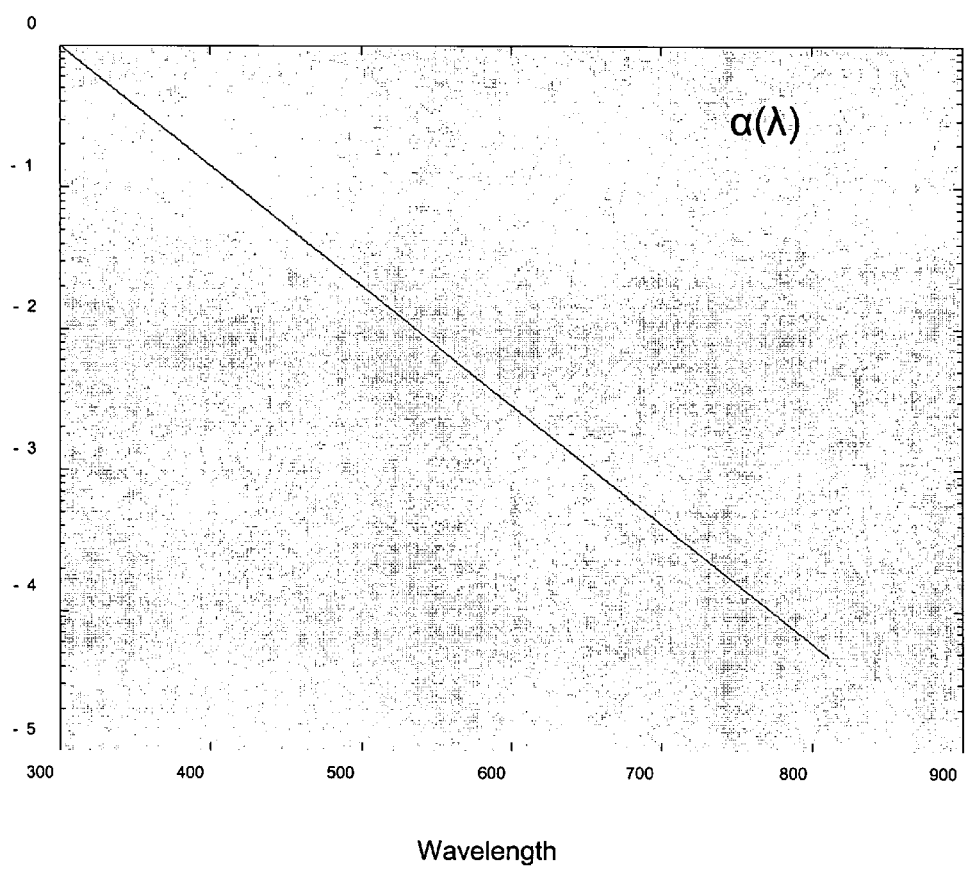
FIG. 3 is an exemplary graph of the absorption coefficient of a thin film absorber according to the present disclosure.
Figure 4:
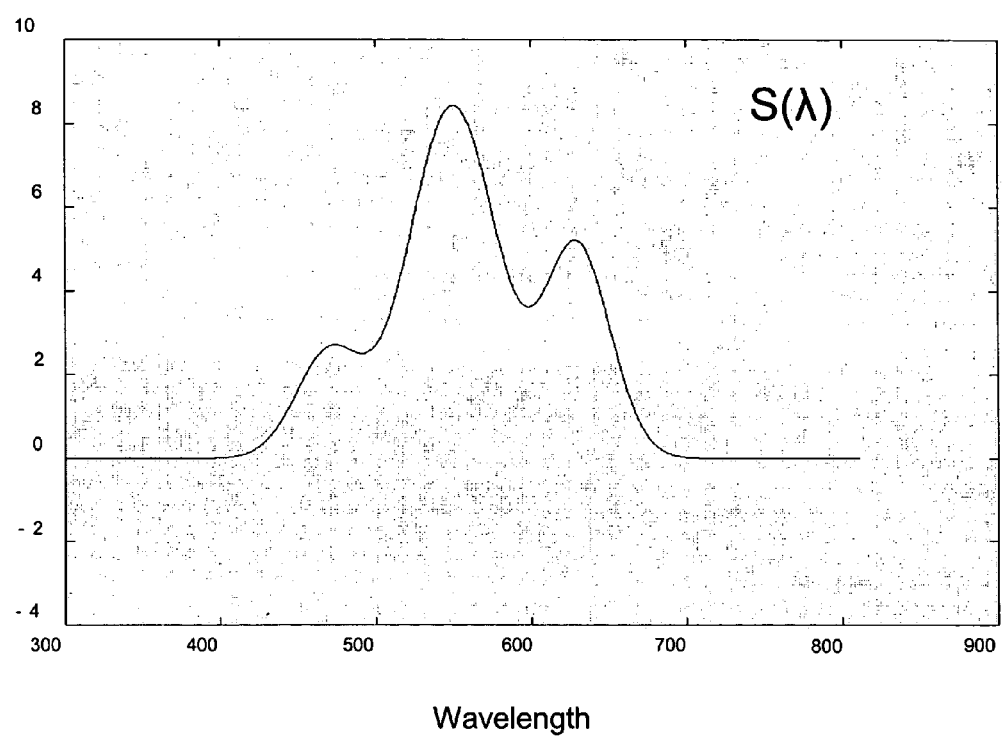
FIG. 4 is an exemplary graph of an intensity spectrum for an input signal.
Figure 5:
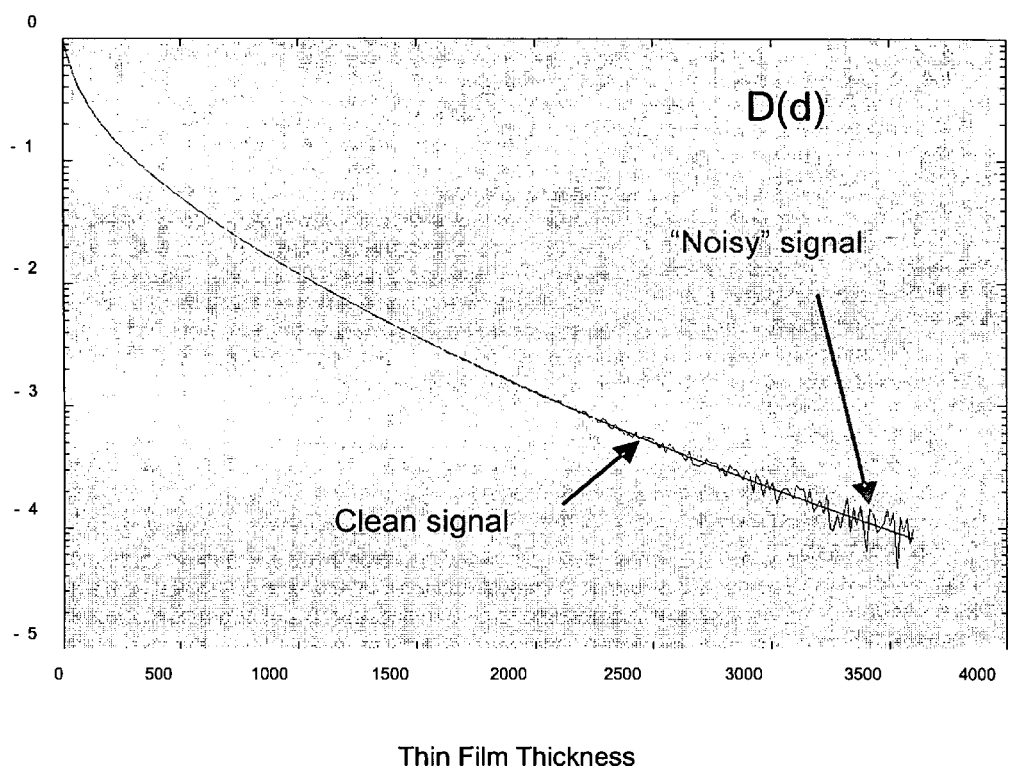
FIG. 5 is an exemplary graph of intensity of an input signal (from FIG. 4) as detected by a photodetector as a function of the thickness of an absorbing thin film (from FIG. 3) that is in the path of the input signal. Both a "clean" signal and a "noisy" signal are depicted.
Figure 6:
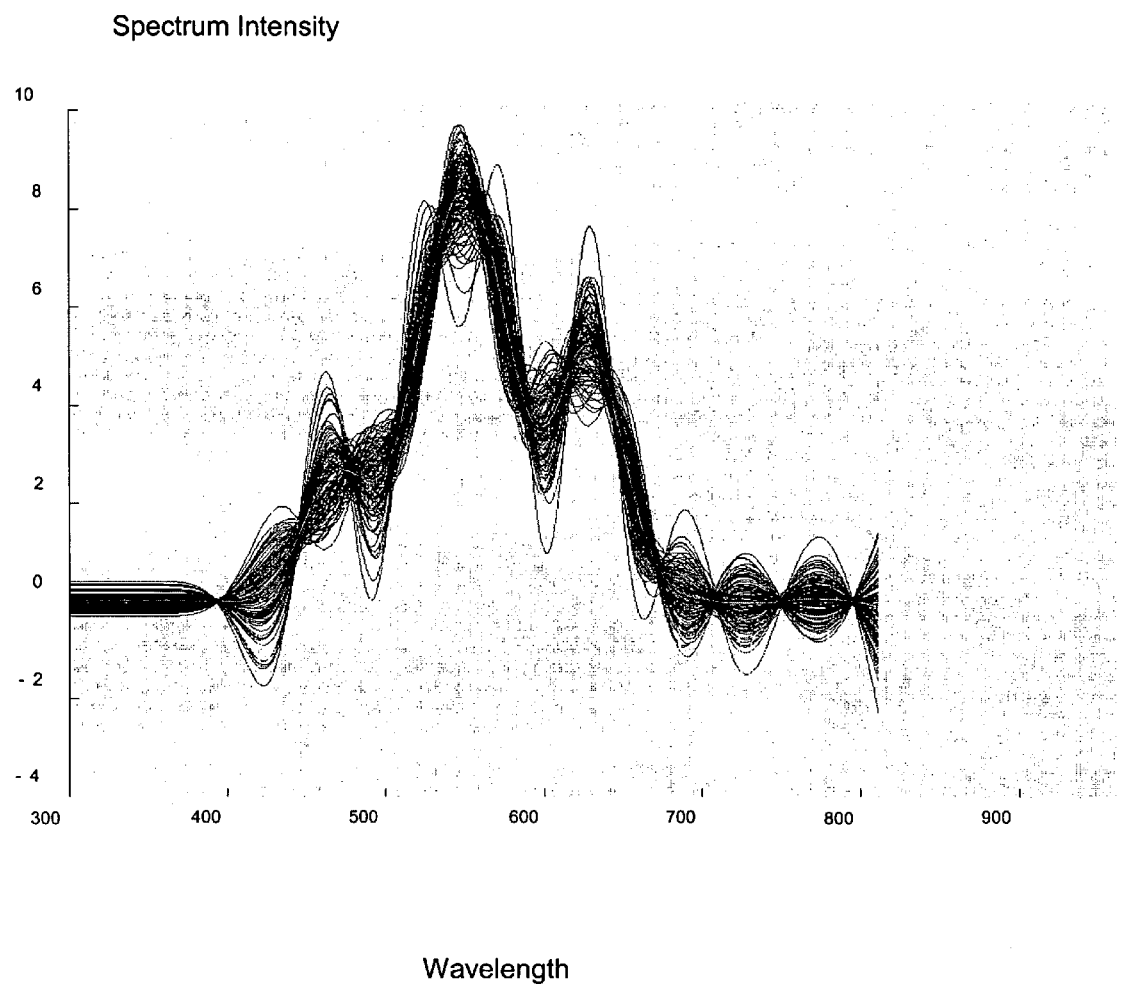
FIG. 6 is an exemplary graph of a reconstructed input signal using the input signal from FIG. 4 with different added noise signals.

The following example design serves as a numerical illustration and is not intended to limit the disclosure in any way. FIG. 2 gives a schematic configuration of a hypothetical device. The absorption coefficient, $\alpha(\lambda)$, is given by, $$\alpha(\lambda_i) = e^{-\beta(\lambda_i - \lambda_{edge})}, \beta = 10, \lambda_{edge} = 300 \text{ nm}$$

where $\lambda_i = \{300 \text{ nm}, 301 \text{ nm}, \ldots, 812 \text{ nm}\}$, providing a wavelength resolution of 1 nm from 300 nm to 812 nm. This profile is shown graphically in FIG. 3. The thicknesses of the thin film absorbers are given by, $$d_i = \frac{d_{\max} i}{i_{\max}}, d_{\max} = 3600, i_{\max} = 511$$

where $i = \{0, 1, \ldots, 511\}$. To test the system, we use an exemplary three-peaked $S(\lambda)$ shown in FIG. 4. The photodetector current signal, without any noise, is shown in FIG. 5. To test the capacity of the system to handle the introduction of noise, random noise is added to $D(d)$, where the random noise has magnitude 5e-5 of the maximum detected signal (as a simulation of photodetector dark current noise), as exemplified in FIG. 5. FIG. 6 illustrates reconstructed $S(\lambda)$ profiles. The original $S(\lambda)$ and the reconstructed signal without any noise are nearly identical on the scale of the graph. Overlaid are one hundred $S(\lambda)$ reconstructed from $D(d)$ with one hundred different random noise signals. The average of these one hundred $S(\lambda)$ is shown and is almost indistinguishable from the original signal.

The above mathematical development illustrates the principle of the device in terms of wavelengths, the most familiar spectral unit. However, an entirely different basis set for the spectral analysis can be used instead. For instance, one could analyze the system in terms of a series of polychromatic spectra (e.g., the absorption spectra of a set of target chemicals), which are referred to herein as the system's characteristic spectra. In this case, one can specify the absorption spectrum of the absorber in terms of these characteristic spectra and construct the transfer matrix with the characteristic spectra as the basis. The spectral analysis that this spectrometer then performs is to determine the composition of the incident signal in terms of the characteristic spectra.

The type of spectrometer presented here can thus analyze the spectral components of an incident signal in terms of any basis set one would like, be it either a set of wavelengths (which is nothing more than a set of comparatively monochromatic spectra) or a set of specially chosen characteristic spectra. This flexibility is a key component of the usefulness of the technology of the disclosure, as for specific, targeted applications, the use of a carefully selected basis set may allow one to obtain all of the desired information with far fewer data points than for a simple wavelength basis.

Figure 7:
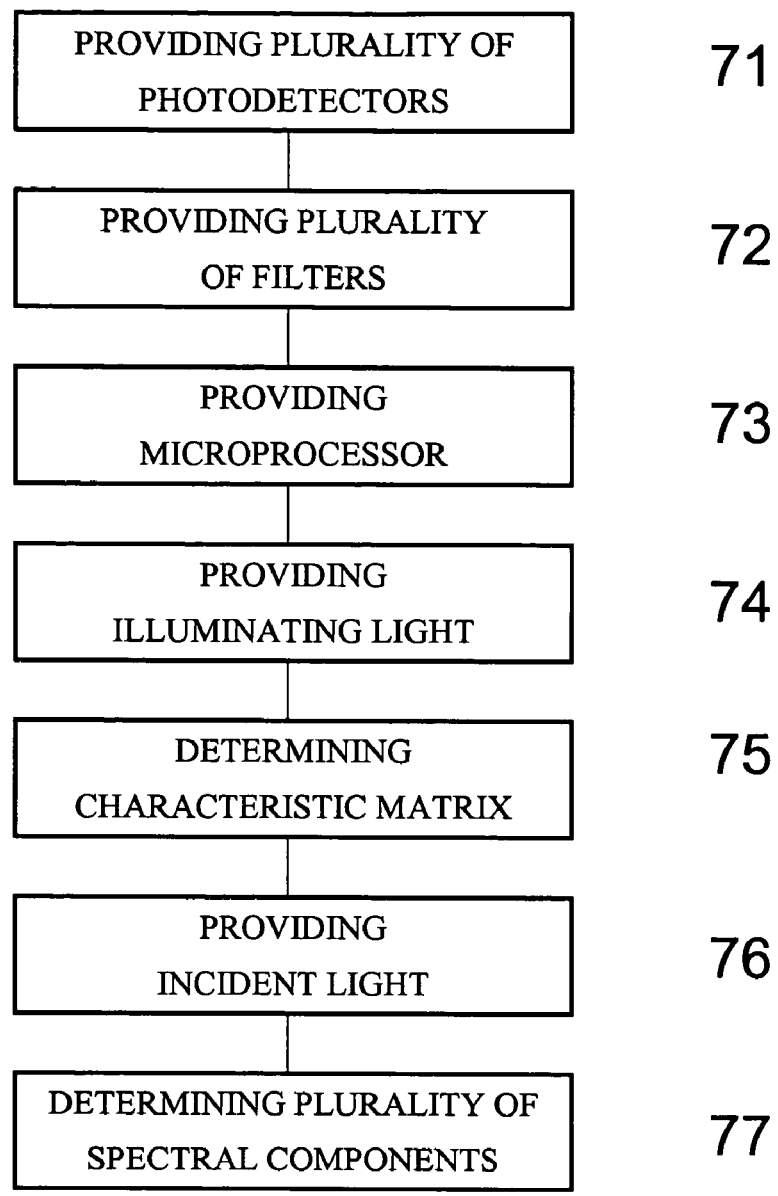
FIG. 7 is a block diagram indicating the major steps for determining spectral components of incident light for an embodiment of the disclosure having plural photodetectors.
Figure 8:
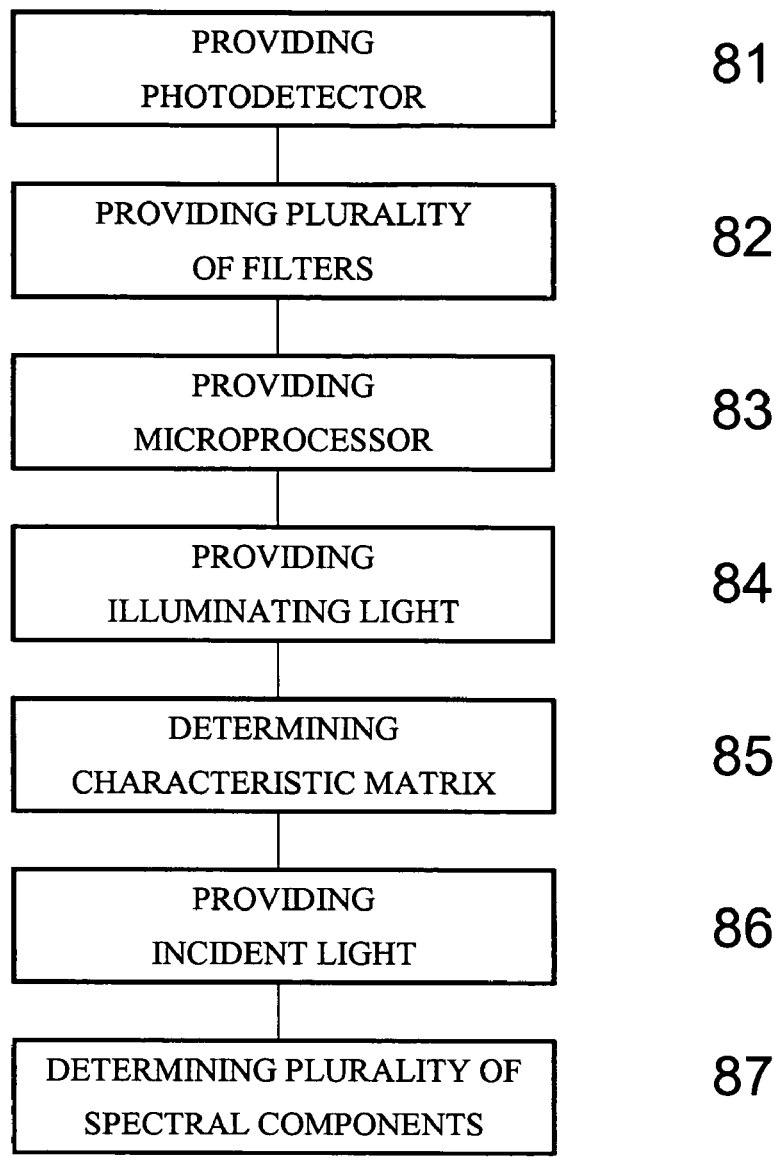
FIG. 8 is a block diagram indicating the major steps for determining spectral components of incident light for an embodiment of the disclosure having a single photodetector.

With reference now to FIGS. 7 and 8, exemplary methods for detecting a plurality of spectral components of incident light will be described. FIG. 7 is a block diagram indicating the major steps for determining spectral components of incident light for an embodiment of the disclosure having plural photodetectors. The method begins with providing plural photodetectors (step 71), providing plural filters (step 72), providing a microprocessor (step 73), and providing illuminating light (step 74). The plural photodetectors are used for detecting light comprised of a plurality of spectral components (which may be, for example, wavelengths) and producing a signal therefrom. The plural filters, which may be thin film absorbing filters with a known absorption coefficient where the absorption coefficient is different for each of the filters, are placed over the photodetectors so that each photodetector has one filter and light passes through the filter to reach the photodetector. The microprocessor receives the signals from the photodetectors. Illuminating light with a known spectral composition is applied to the system so that the photodetectors receive the illuminating light via the filters and produce a first signal that is a function of an attribute of the illuminating light. The first signal is received by the microprocessor which determines the characteristic matrix for the illuminating light (step 75). Incident light with an unknown spectral composition is then applied to the system (step 76) so that the photodetectors receive the incident light via the filters and produce a second signal that is a function of an attribute of the incident light. The second signal is received by the microprocessor which determines the spectral components of the incident light using the characteristic matrix determined for the illuminating light (step 77).

FIG. 8 is a block diagram indicating the major steps for determining spectral components of incident light for an embodiment of the disclosure having a single photodetector. The steps are similar to those described above for FIG. 7. The method begins with providing a photodetector (step 81), providing plural filters (step 82), providing a microprocessor (step 83), and providing illuminating light (step 84). The photodetector is used for detecting light comprised of a plurality of spectral components (which may be, for example, wavelengths) and producing a signal therefrom. The plural filters, which may be thin film absorbing filters with a known absorption coefficient where the absorption coefficient is different for each of the filters, are sequentially passed across the photodetector so that light passes through one of the filters to reach the photodetector. The microprocessor receives the signals from the photodetector. Illuminating light with a known spectral composition is applied to the system so that the photodetector receives the illuminating light via the filters and produces a first signal that is a function of an attribute of the illuminating light. The first signal is received by the microprocessor which determines the characteristic matrix for the illuminating light (step 85). Incident light with an unknown spectral composition is then applied to the system (step 86) so that the photodetector receives the incident light via the filters and produces a second signal that is a function of an attribute of the incident light. The second signal is received by the microprocessor which determines the spectral components of the incident light using the characteristic matrix determined for the illuminating light (step 87).

The slim format spectrometer as disclosed herein is uniquely well-suited for applications in which a few different known spectra are to be identified and quantified, and where cost, size, and durability are critical. For instance, such spectrometers could be used in smoke detectors, transforming them into sophisticated environmental sensing hubs while still maintaining low cost. While smoke detectors already include simple optical sensors for detecting light scattering (a signature of smoke), recently companies have recognized the advantage of resolving different wavelengths to achieve equal sensitivity to both white and black smoke. With the use of the apparatus and method disclosed herein, however, such smoke detectors would gain the ability to not only identify the presence or absence of smoke, but to also obtain information about the smoke contents, and thereby the type of fire. Such information could be relayed directly to response teams to aid in the management of the emergency. More generally, such detectors could monitor the presence or absence of a variety of airborne chemicals, and through the use of a computer interface, could be monitored in real time. This provides just one example of how the disclosed apparatus and method could be utilized to make optical spectroscopy part of a ubiquitous sensing system, something only possible with extremely small and low cost technology.

Medical applications are also promising. Already, opto-electronic sensors are employed for pulse oximetry, blood glucose monitoring, and urine analysis. Presently, these systems are highly targeted, providing useful but limited functionality (i.e. single component sensitivity). However, with an optical spectrometer, one could greatly expand the capabilities of these devices, turning them into general purpose, and extremely low cost, medical diagnostic tools.

Pulse oximetry systems utilize two light emitting diodes (LEDs), one infrared and one visible, and a light sensor, and the package is clipped onto one's earlobe (or over one's finger. By monitoring the light absorption, the blood levels of oxy-hemoglobin (which is oxygenated) can be determined noninvasively. By expanding the system to utilize broadband LEDs and a spectrometer one can obtain far more information about one's blood chemistry (allowing for the measurement of a range of different chemicals), and this can be done with little or no increase in package size or cost.

Higher sensitivity, ex vitro blood and urine analysis could also be performed using a similar device. The economics in this case, however, are different than in the previous example, as optical spectrometry is already utilized for these tasks in medical labs around the world. The apparatus and method herein disclosed would not be targeted to supplant these devices; rather it would make possible new devices that are so portable and inexpensive that a doctor could provide them to all his patients. This would radically increase the range of medical services that could be provided remotely or autonomously, and market precedents already exist for the successful application of such an approach. Diabetes products under development have demonstrated a highly efficacious treatment in which the patient uses a real-time blood glucose monitor linked to a computer, which has algorithms to turn this data into useful instructions for the patient's food and exercise regimen on a daily basis. In addition, doctors can be made more rapidly aware of emergencies, as well as obtain better blood glucose level monitoring without patient visits. In this case, the patient receives far better results (which saves insurance companies money in future care), while simultaneously saving time for both the patient and the doctor. Such a model can be applied generally, limited only by the range of easily monitored health parameters, and the presently described apparatus and method would greatly expand that range.

Finally, in addition to the examples described above, the presently described apparatus and method has the potential to make possible chip-level integration of optical spectroscopy, a key component in the continuing development of the lab-on-a-chip (LOC) products used in the pharmaceuticals and health care industries. No existing technology, even at great cost, can provide integrated optical spectrometers for use in a microfluidic platform, which remains a major limitation in the capabilities of LOCs. However, since our approach can be realized using existing silicon technologies and integrated thin films, fully monolithic integration into LOCs would be possible for the first time.

The embodiments disclosed herein are exemplary and non-limiting. While the principles of the disclosure have been disclosed in relation to specific exemplary embodiments, it is noted that the principles of the invention are not limited thereto and include all modification and variation to the specific embodiments disclosed herein.

We claim:

1. An apparatus for detecting a plurality of spectral components of incident light, comprising:
    a plurality of photodetectors each for detecting incident light comprised of a plurality of spectral components and producing a signal therefrom; and
    a plurality of single layer filters each with a known absorption coefficient which is different from the absorption coefficient of the other filters,
    wherein for each of said photodetectors one of said filters is disposed such that the light incident to said photodetector passes through said one filter, and
    wherein said filters are comprised of the same material.

2. The apparatus of claim 1 wherein the spectral components comprise monochromatic spectra.

3. The apparatus of claim 1 wherein the spectral components comprise polychromatic spectra.

4. The apparatus of claim 1 further comprising a microprocessor for receiving said signals from said plural photodetectors and determining therefrom the plurality of spectral components of the incident light.

5. The apparatus of claim 4 wherein the number of photodetectors equals the number of filters which is not less than the number of spectral components determined from the incident light.

6. The apparatus of claim 1 wherein the absorption coefficient of the plural filters changes monotonically over the wavelength range of said plurality of spectral components.

7. The apparatus of claim 1 wherein the different absorption coefficient of said filters is provided by a difference in the thicknesses of said filters.

8. The apparatus of claim 1 wherein said plural filters are each comprised of a material including a dye and wherein the concentration of the dye in said material is different for each of said plural filters.

9. The apparatus of claim 1 wherein said plural filters are each comprised of an organic film.

10. The apparatus of claim 1 wherein said plural filters are each comprised of an inorganic film.

11. The apparatus of claim 1 wherein said plural filters are each comprised of a nanostructured film.

12. An apparatus for detecting a plurality of spectral components of incident light, comprising:
    a photodetector for detecting incident light comprised of a plurality of spectral components and producing a signal therefrom; and
    a plurality of single layer filters each with a known absorption coefficient which is different from the absorption coefficient of the other filters,
    wherein said filters are sequentially passed across said photodetector such that the light incident to said photodetector sequentially passes through said filters, and
    wherein said filters are comprised of the same material.

13. The apparatus of claim 12 wherein the spectral components comprise monochromatic spectra.

14. The apparatus of claim 12 wherein the spectral components comprise polychromatic spectra.

15. The apparatus of claim 12 further comprising a microprocessor for receiving said signal from said photodetector and determining therefrom the plurality of spectral components of the incident light.

16. The apparatus of claim 15 wherein the number of filters is not less than the number of spectral components determined from the incident light.

17. The apparatus of claim 12 wherein the absorption coefficient of the plural filters changes monotonically over the wavelength range of said plurality of spectral components.

18. The apparatus of claim 12 wherein the different absorption coefficient of said filters is provided by a difference in the thicknesses of said filters.

19. The apparatus of claim 12 wherein said plural filters are each comprised of a material including a dye and wherein the concentration of the dye in said material is different for each of said plural filters.

20. The apparatus of claim 12 wherein said plural filters are each comprised of an organic film.

21. The apparatus of claim 12 wherein said plural filters are each comprised of an inorganic film.

22. The apparatus of claim 12 wherein said plural filters are each comprised of a nanostructured film.

23. A method for detecting a plurality of spectral components of incident light, the method comprising the steps of:
    providing a plurality of photodetectors each for detecting incident light comprised of a plurality of spectral components and producing a signal therefrom;
    providing a plurality of filters each with a known absorption coefficient which is different from the absorption coefficient of the other filters, wherein for each of said photodetectors one of said filters is disposed such that the light incident to said photodetector passes through said one filter;
    providing a microprocessor for receiving said signals from said plural photodetectors;
    providing illuminating light with a known spectral composition;
    determining a characteristic matrix for the illuminating light using said microprocessor;
    providing incident light with an unknown spectral composition;
    determining the plurality of spectral components of the incident light using said microprocessor and said characteristic matrix.

24. The method of claim 23 wherein the illuminating light is substantially monochromatic.

25. A method for detecting a plurality of spectral components of incident light, the method comprising the steps of:
    providing a photodetector for detecting incident light comprised of a plurality of spectral components and producing a signal therefrom;
    providing a plurality of filters each with a known absorption coefficient which is different from the absorption coefficient of the other filters, wherein said filters are sequentially passed across said photodetector such that the light incident to said photodetector sequentially passes through said filters;
    providing a microprocessor for receiving said signals from said photodetector;
    providing illuminating light with a known spectral composition;

determining a characteristic matrix for the illuminating light using said microprocessor;

providing incident light with an unknown spectral composition;

determining the plurality of spectral components of the incident light using said microprocessor and said characteristic matrix.

26. The method of claim 25 wherein the illuminating light is substantially monochromatic.

27. An apparatus for detecting a plurality of spectral components of incident light, comprising:

a plurality of photodetectors each for detecting incident light comprised of a plurality of spectral components and producing a signal therefrom;

a plurality of single layer filters each with a known absorption coefficient which is different from the absorption coefficient of the other filters, wherein for each of said photodetectors one of said filters is disposed such that the light incident to said photodetector passes through said one filter; and a microprocessor for receiving said signals from said plural photodetectors and determining therefrom the plurality of spectral components of the incident light, wherein the number of photodetectors equals the number of filters which is not less than the number of spectral components determined from the incident light, and wherein said filters are comprised of the same material where the absorption coefficient of the plural filters changes monotonically over the wavelength range of said plurality of spectral components, and wherein the different absorption coefficient of said filters is provided by a difference in the thicknesses of said filters.

28. The apparatus of claim 27 wherein the spectral components comprise monochromatic spectra.

29. The apparatus of claim 27 wherein the spectral components comprise polychromatic spectra.

* * * * *